United States Patent
Bonrath et al.

(10) Patent No.: US 6,369,242 B2
(45) Date of Patent: Apr. 9, 2002

(54) TOCOPHEROL MANUFACTURE BY TRIS (PERFLUOROHYDROCARBYLSULPHONYL) METHANE OR METAL METHIDES THEREOF

(75) Inventors: Werner Bonrath, Freiburg; Alois Haas, Bochum; Eike Hoppmann, Leipzig; Thomas Netscher, Bad Krozingen, all of (DE); Horst Pauling, Aesch (CH)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/802,272

(22) Filed: Mar. 8, 2001

(30) Foreign Application Priority Data

Mar. 17, 2000 (EP) ............................. 00105672

(51) Int. Cl.[7] ............................. C07D 311/04
(52) U.S. Cl. .................................... 549/408
(58) Field of Search ................... 549/408; 514/458

(56) References Cited

U.S. PATENT DOCUMENTS 5,273,840 A  12/1993  Dominey
5,554,664 A   9/1996  Lamanna et al.

FOREIGN PATENT DOCUMENTS

| EP | 0 658 552 A1 | 6/1995 |
| EP | 0 949 255 A1 | 10/1999 |
| EP | 1 000 940 A1 | 5/2000 |
| WO | WO 98/21197 | 5/1998 |

OTHER PUBLICATIONS

Nishikido, et al., "Scandium and Ytterbium Tris(perfluorobutanesulfonyl)methide Complexes: Extremely Efficient Lewis Acid Catalysts," *Synlett*, No. 12, pp. 1990–1992 (1999).

Waller, et al., "Tris(trifluoromethanesulfonylmethide ("Triflide") Anion: Convenient Preparation, X–ray Crystal Structures, and Exceptional Catalytic Activity as a Counterion with Ytterbium(III) and Scandium(III)," *J. Org. Chem.*, vol. 64, pp. 2910–2913 (1999).

*Primary Examiner*—T. A. Solola
*Assistant Examiner*—Joseph Murray
(74) *Attorney, Agent, or Firm*—Bryan Cave LLP

(57) ABSTRACT

A method of making (all-rac.)-α-tocopherol by the acid-catalyzed condensation of trimethylhydroquinone with isophytol or phytol wherein the condensation is carried out in the presence of a tris(perfluoroalkanesulphonyl or pentafluorobenzenesulphonyl)methane or a metal salt thereof as the catalyst in an organic solvent. In addition to the metal salt, a Bronsted acid, e.g. sulfuric acid, phosphoric acid or p-toluenesulphonic acid, may be used as a co-catalyst. The product of the method of making is the most active member of the vitamin E group.

15 Claims, No Drawings

TOCOPHEROL MANUFACTURE BY TRIS (PERFLUOROHYDROCARBYLSULPHONYL) METHANE OR METAL METHIDES THEREOF

FIELD OF THE INVENTION

The present invention relates to a novel process for the manufacture of (all-rac.)-α-tocopherol by the acid-catalyzed condensation of trimethylhydroquinone (TMHQ) with isophytol (IP) or phytol (PH) in a solvent. (All-rac.)-α-tocopherol, ("d,l-α-tocopherol") is a diastereoisomeric mixture of 2,5,7,8-tetramethyl-2-(4',8',12'-trimethyl-tridecyl)-6-chromanol (α-tocopherol), which is the most active and most industrially important member of the vitamin E group.

BACKGROUND OF THE INVENTION

Many processes for the manufacture of d,l-α-tocopherol by the condensation of TMHQ with IP or PH in the presence of a catalyst or catalyst system and in a solvent or solvent system are described in the literature. These processes go back to the work of Karrer et al., Bergel et al., and Smith et al. (see Helv. Chim. Acta 21, 520 et seq. (1938), Nature 142, 36 et seq. (1938) and, respectively, Science 88, 37 et seq. (1938) and J. Am. Chem. Soc. 61, 2615 et seq. (1939)). While Karrer et al. carried out the synthesis of d,l-α-tocopherol from TMHQ and phytyl bromide in the presence of anhydrous zinc chloride ($ZnCl_2$; a Lewis acid), Bergel et al. and Smith et al. used TMHQ and PH as starting materials. In the following years mainly modifications, e.g. alternative solvents and Lewis acids, were developed. From the work of Karrer et al. a technically interesting process for the manufacture of d,l-α-tocopherol which was based on the condensation of TMHQ with IP in the presence of the catalyst system $ZnCl_2$/hydrochloric acid (HCl) (Karrer et al., U.S. Pat. No. 2,411,969) was developed in 1941. Later publications, e.g. Japanese Patent Publications (Kokai) 54380/1985, 64977/1985 and 226979/1987 (Chemical Abstracts (C.A.) 103, 123731s (1985), C.A. 103, 104799d (1985) and, respectively, C.A. 110, 39217r (1989)), describe this condensation in the presence of zinc and/or $ZnCl_2$ and a Bronsted (protonic) acid, such as a hydrohalic acid, e.g. HCl, trichloroacetic acid, acetic acid and the like, especially $ZnCl_2$/HCl, as the catalyst system. The disadvantages of these and further published processes featuring $ZnCl_2$ in combination with a Bronsted acid are the corrosive properties of the acids and the contamination of the waste water with zinc ions as a result of the large amount of $ZnCl_2$ required for the catalysis.

The manufacture of d,l-(α-tocopherol by the reaction of TMHQ with phytyl chloride, PH or IP in the presence of boron trifluoride ($BF_3$) or its etherate ($BF_3.Et_2O$) is described in German Patents 960720 and 1015446 and Nelan, U.S. Pat. No. 3,444,213. However, $BF_3$ also has corrosive properties.

Also, the condensation of TMHQ with IP or PH in the presence of a Lewis acid, e.g. $ZnCl_2$, $BF_3$ or aluminum trichloride ($AlCl_3$), a strong acid, e.g. HCl, and an amine salt as the catalyst system is described in European Patent Publication (EP) 100471. In an earlier patent publication, DOS 2606830, the IP or PH is pretreated with ammonia or an amine before the condensation with TMHQ in the presence of $ZnCl_2$ and an acid is effected. In both cases corrosion problems occur.

A further interesting method for the manufacture of d,l-α-tocopherol from TMHQ and IP used an isolated TMHQ-$BF_3$ or -$AlCl_3$ complex and a solvent mixture featuring a nitro compound (DOS 1909164). This process avoids to a large extent the formation of undesired by-products because it involves mild reaction conditions. The yield of d,l-α-tocopherol, based on IP and the use of the solvent mixture methylene chloride/nitro-methane, is given as 77%. However, the use of such a solvent mixture is disadvantageous.

The manufacture of d,l-α-tocopherol by the condensation of TMHQ with IP using cation exchange resin complexes of metal ions ($Zn^{2+}$, $Sn^{2+}$ and $Sn^{4+}$) is disclosed in Bull. Chem. Soc. Japan 50, 2477–2478 (1977). Among other disadvantages, it gives the product in unsatisfactory yields.

The use of macroreticular ion exchangers, e.g. Amberlyst® 15, as the catalyst for the condensation of TMHQ with IP is described in Moroe et al., U.S. Pat. No. 3,459,773. However, the d,l-α-tocopherol is not produced in satisfactory purity.

EP 603695 describes the manufacture of d,l-α-tocopherol in liquid or supercritical carbon dioxide by the condensation of TMHQ with IP or PH in the presence of acidic catalysts, such as $ZnCl_2$/HCl and ion exchangers. The reported yields are unsatisfactory.

The condensation in the presence of a catalyst system which consists of iron(II) chloride, metallic iron and HCl gas or aqueous solution is described in DOS 2160103 and Heinrich et al., U.S. Pat. No. 3,789,086. The formation of less by-products is advantageous compared with the aforementioned process using $ZnCl_2$/HCl. However, corrosion problems and chloride contamination are disadvantageous.

An interesting alternative for the condensation of TMHQ with IP to d,l-α-tocopherol uses trifluoroacetic acid or its anhydride as the catalyst (EP 12824). Although in this process the avoidance of HCl is achieved, the catalyst is expensive.

The use of the heteropoly acid 12-tungstophosphoric or 12-tungstosilicic acid as the catalyst for the condensation of TMHQ with IP was described for the first time in React. Kinet. Catal. Lett. 47 (1), 59–64 (1992). d,l-α-Tocopherol could be obtained, using various solvents, in about 90% yield.

A further process described in the literature (EP 658552; Bull. Chem. Soc. Japan 68, 3569–3571 (1995)) for the synthesis of d,l-α-tocopherol is based on the use of a scandium, yttrium or lanthanide fluorosulphonate, nitrate or sulphate, e.g. scandium trifluoromethanesulphonate, as the catalyst for the condensation. With up to about 10% excess of IP this process gives yields up to 98%.

The use of ion-exchanged bentonite, montmorillonite or saponite through treatment with e.g. scandium chloride and other metal salts (yttrium, lanthanum, etc.) as the catalyst for the condensation of TMHQ with IP or PH has as a disadvantage the need for a large amount of catalyst (EP 677520; Bull. Chem. Soc. Japan 69, 137–139 (1996)).

According to the Examples of EP 694 541, the condensation of TMHQ with IP to α-tocopherol can be achieved in high yields and with a high product purity when such solvents as carbonate esters, fatty acid esters and certain mixed solvent systems are employed, the exemplified catalysis being effected by $ZnCl_2$/HCl. Disadvantages in this process are, in addition to the contamination of the waste water by zinc ions, the usual large "catalyst amount" of $ZnCl_2$ used.

According to WO 97/28151, the acid-catalyzed condensation of TMHQ with IP can be performed using a cyclic carbonate or α-lactone as the solvent. The preferred catalyst is a mixture of orthoboric acid and oxalic, tartaric or citric acid, or boron trifluoride etherate.

WO 98/21197 describes the manufacture of d,l-α-tocopherol from TMHQ and IP using bis (trifluoromethylsulphonyl)amine or a metal salt thereof optionally together with a strong Bronsted acid, as catalyst in such types of aprotic solvents as aliphatic and cyclic ketones or esters, and aromatic hydrocarbons.

From the forgoing review it is evident that most of the previously known processes have considerable disadvantages. Thus, corrosion problems occur in all processes in which such acid catalysts as boron trifluoride are used. Toxicity problems with the boron trifluoride adducts also occur, and when iron or zinc is used there is a contamination of the waste water with the metal ions which is today no longer acceptable. In some processes the formation of undesired by-products, e.g. phytyltoluene and chlorophytols, is an especially serious problem.

SUMMARY OF THE INVENTION

An object of the present invention is to provide a process for the manufacture of (all-rac.)-α-tocopherol by the condensation of trimethylhydroquinone with isophytol or phytol in the presence of a catalyst and in a solvent which does not have the disadvantages of previously known procedures. In this respect, it is necessary that the catalyst used has no, or at least a much reduced, corrosive action, is non-toxic, does not contaminate the environment and catalyzes the desired reaction as selectively as possible and in high yields. Furthermore, the catalyst should display its activity in small, catalytic amounts and should be readily separable and reusable several times.

Another object of the invention is a method of making (all-rac.)-α-tocopherol. This method includes: reacting trimethylhydroquinone (TMHQ) with isophytol (IP) or phytol (PH) in an organic solvent and in the presence of a tris (perfluoroalkanesulphonyl)methane, a tris (pentafluorobenzenesulphonyl)methane, a metal tris (perfluoroalkanesulphonyl)methide, or a metal tris (pentafluorobenzenesulphonyl)methide catalyst of formula I:

$$[(R^1SO_2)_3C]_x R^2 \qquad \qquad I$$

wherein
$R^1$ is a perfluoroalkyl group $C_nF_{2n+1}$ or pentafluorophenyl,
$R^2$ is a proton or a metal cation selected from the group consisting of boron, magnesium, aluminium, silicon, scandium, titanium, vanadium, vanadyl, manganese, iron, cobalt, nickel, copper, zinc, yttrium, zirconium, rhodium, palladium, silver, tin, lanthanum, cerium, praseodymium, neodymium, europium, dysprosium, ytterbium, hafnium, platinum, and gold,
n is an integer from 1 to 10, and
x is the corresponding valency of the proton (1) or metal cation (1, 2, 3, or 4);
and isolating the (all-rac.)-α-tocopherol.

Another embodiment of the invention is an acid-catalyzed process for producing (all-rac.)-α-tocopherol. This process includes forming a reaction mixture comprising trimethyl-hydroquinone (TMHQ) with isophytol (IP) or phytol (PH), an organic solvent, and a tris(perfluoroalkanesulphonyl)methane, a tris(pentafluorobenzenesulphonyl)methane, a metal tris(perfluoroalkanesulphonyl)methide, or a metal tris (pentafluorobenzenesulphonyl)methide catalyst of formula I:

$$[(R^1SO_2)_3C]_x R^2 \qquad \qquad I$$

wherein
$R^1$ is a perfluoroalkyl group $C_nF_{2n+1}$ or pentafluorophenyl,
$R^2$ is a proton or a metal cation selected from the group consisting of boron, magnesium, aluminium, silicon, scandium, titanium, vanadium, vanadyl, manganese, iron, cobalt, nickel, copper, zinc, yttrium, zirconium, rhodium, palladium, silver, tin, lanthanum, cerium, praseodymium, neodymium, europium, dysprosium, ytterbium, hafnium, platinum, and gold,
n is an integer from 1 to 10, and
x is the corresponding valency of the proton (1) or metal cation (1,2,3 or 4);
and isolating the (all-rac.)-α-tocopherol.

A further embodiment of the invention is a reaction mixture containing:
(a) trimethylhydroquinone (TMHQ),
(b) isophytol (IP) or phytol (PH) in an organic solvent, and
(c) a tris(perfluoroalkanesulphonyl)methane, a tris (pentafluorobenzenesulphonyl)methane, a metal tris (perfluoroalkanesulphonyl)methide, or a metal tris-(pentafluorobenzenesulphonyl)methide catalyst of formula I:

$$[(R^1SO_2)_3C]_x R^2 \qquad \qquad I$$

wherein
$R^1$ is a perfluoroalkyl group $C_nF_{2n+1}$ or pentafluorophenyl,
$R^2$ is a proton or a metal cation selected from the group consisting of boron, magnesium, aluminium, silicon, scandium, titanium, vanadium, vanadyl, manganese, iron, cobalt, nickel, copper, zinc, yttrium, zirconium, rhodium, palladium, silver, tin, lanthanum, cerium, praseodymium, neodymium, europium, dysprosium, ytterbium, hafnium, platinum, and gold,
n is an integer from 1 to 10, and
x is the corresponding valency of the proton (1) or metal cation (1,2,3 or 4).

In this reaction mixture, (all-rac.)-α-tocopherol is formed by an acid-catalyzed condensation.

DETAILED DESCRIPTION OF THE INVENTION

The objects of the present invention are achieved by carrying out the condensation of trimethylhydroquinone with isophytol or phytol in the presence of a so-called CH-acidic compound or a metal salt thereof, which is more particularly a tris(perfluoroalkanesulphonyl or pentafluorobenzenesulphonyl)methane or a metal tris (perfluoroalkanesulphonyl or pentafluorobenzenesulphonyl) methide, in an organic solvent.

The condensation itself is represented in the following Reaction Scheme, showing the reaction with IP only.

Reaction Scheme

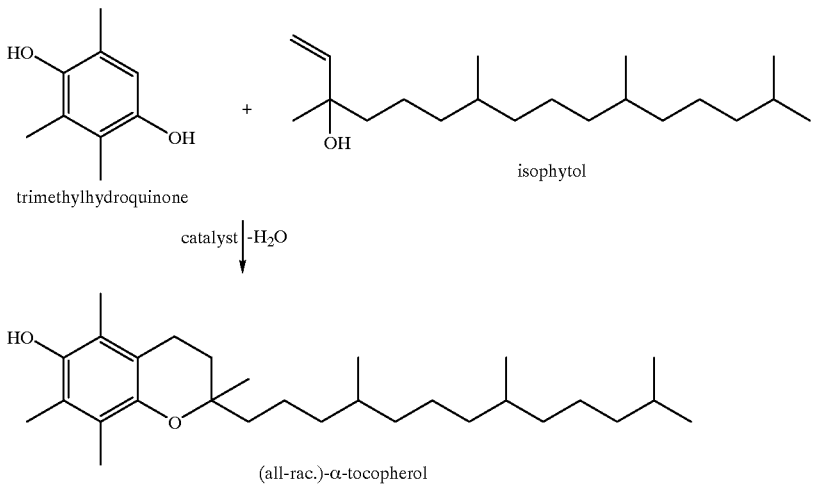

(all-rac.)-α-tocopherol

Accordingly, the process in accordance with the invention for the manufacture of (all-rac.)-α-tocopherol by the catalyzed condensation of trimethylhydroquinone with isophytol or phytol, is characterized by carrying out the condensation in the presence of a tris(perfluoroalkanesulphonyl or pentafluorobenzenesulphonyl)methane or a metal tris (perfluoroalkanesulphonyl or pentafluorobenzenesulphonyl) methide, of the general formula $$[(R^1SO_2)_3C]_x R^2 \qquad\qquad I$$

wherein $R^1$ is a perfluoroalkyl group $C_nF_{2n+1}$ or pentafluorophenyl, $R^2$ is a proton or a metal cation selected from the group consisting of boron, magnesium, aluminium, silicon, scandium, titanium, vanadium, vanadyl, manganese, iron, cobalt, nickel, copper, zinc, yttrium, zirconium, rhodium, palladium, silver, tin, lanthanum, cerium, praseodymium, neodymium, europium, dysprosium, ytterbium, hafnium, platinum and gold, each in the cationic form, n is an integer from 1 to 10 and x is the corresponding valency of the proton (1) or metal cation (1,2,3 or 4), as the catalyst in an organic solvent.

Some of the CH-acidic compounds and their metal salts of formula I are known compounds. Thus, in Inorg. Chem. 27, 2135–2137 (1988) K. Seppelt and L. Turowsky describe for the first time the preparation of tris (trifluoromethanesulphonyl)methane, $(CF_3SO_2)_3CH$, and of four salts thereof, viz. the potassium, rubidium, silver and cesium salts. The lithium and further metal salts of $(CF_3SO_2)_3CH$ and other tris(perfluoroalkanesulphonyl) methides and their preparation are described in Dominey, U.S. Pat. No. 5,273,840. Also developing the original work of Seppelt and Turowsky, F. J. Waller et al. describe in J. Org. Chem. 64, 2910–2913 (1999) the further preparation of $(CF_3SO_2)_3CH$ and its cesium salt, and also the preparation of the corresponding scandium and ytterbium salts. In Synlett 1999, No. 12, 1990–1992, J. Nishikido et al. describe the preparation of scandium, yttrium and, in general, lanthanide (III) tris(perfluorobutanesulphonyl)methide complexes. Further literature concerning the preparation of these and further metal tris(perfluoroalkanesulphonyl)methides includes Lamanna et al., U.S. Pat. No. 5,554,664 and the many references mentioned in this and in other aforementioned publications.

The tris(perfluoroalkanesulphonyl or pentafluorobenzenesulphonyl)methanes or metal salts thereof embraced by formula I and used as the catalysts in the process of the present invention can be produced according to such published methods, or in the case of those methanes or metal salts thereof which may still not be known, according to analogous methods.

In the case of the metal tris(perfluoroalkanesulphonyl or pentafluorobenzenesulphonyl)methides (the metal salts), this catalyst can be used together with a strong Bronsted acid as a co-catalyst in the process of the present invention. The Bronsted acid present in such a catalyst system can be an inorganic or organic acid, examples of which are sulfuric acid, phosphoric acid, and p-toluenesulphonic acid. In the case of using a lithium salt as the catalyst of formula I ($R^2$ being the lithium cation), the use of a Bronsted acid as a co-catalyst is particularly preferred.

Solvents which can be used in the present invention are polar or non-polar organic solvents. Suitable classes of polar solvents include aliphatic and cyclic ketones, e.g. isobutyl methyl ketone and diethyl ketone and, respectively, cyclopentanone and isophorone; and aliphatic and cyclic esters, e.g. ethyl acetate and isopropyl acetate, and, respectively, γ-butyrolactone, ethylene carbonate and propylene carbonate. Suitable classes of non-polar solvents include aliphatic hydrocarbons, e.g. hexane, heptane and octane, and aromatic hydrocarbons, e.g. benzene, toluene and the xylenes. The condensation can be effected in a single solvent phase, e.g. in toluene alone as the solvent, or in a biphasic solvent system, e.g. in ethylene carbonate and hexane.

The method is conveniently effected at temperatures from about 60° C. to about 150° C., preferably from about 100° C. to about 120° C.

Furthermore, the molar ratio of trimethylhydroquinone to isophytol/phytol present in the reaction mixture is from about 1.3:1 to about 2.5:1, preferably from about 1.5:1 to about 2.2:1, such as for example about 2:1.

The amount of catalyst of formula I used is such that the molar ratio of catalyst to the educt (trimethylhydroquinone or isophytol/phytol) which is in the lesser molar amount (generally the isophytol or phytol) is from about 0.1:100 to about 2:100, i.e. is from about 0.1 mole % to about 2 mole %.

Conveniently about 10–100 ml, preferably about 30–60 ml, of organic solvent are used per 10 mmol of isophytol or phytol, whichever is employed.

If the process reaction is carried out in a biphasic solvent system, especially one consisting of a polar solvent, e.g. a cyclic carbonate such as ethylene or propylene carbonate, and a non-polar solvent, e.g. an aliphatic hydrocarbon such as hexane, then the volume ratio of the non-polar solvent to the polar solvent is from about 0.3:1 to about 5:1, preferably from about 1:1 to about 3:2.

Moreover, the process reaction may be carried out under an inert gas atmosphere, preferably gaseous nitrogen or argon.

The reaction generally lasts for about 0.2–20 hours, preferably about 0.5–1 hour.

The method in accordance with the invention can be carried out batchwise or continuously. For example, isophytol or phytol may be added, as such or in solution, portion-wise to a suspension or solution of the trimethylhydroquinone and the catalyst. The rate at which the isophytol or phytol is added is not critical. Conveniently, isophytol/phytol is added continuously over a period 0.5 to 5 hours. After completion of the isophytol/phytol addition and an appropriate subsequent reaction period the working-up is effected by procedures conventionally used in organic chemistry.

If desired, the obtained (all-rac.)-α-tocopherol can be converted into its acetate, succinate, poly(oxyethylene) succinate, nicotinate and further known application forms by standard procedures (See, for example, the 5th Edition of Ullmann's Encyclopedia of Industrial Chemistry, Vol. A 27, pages 484–485 (VCH Verlagsgesellschaft mbH, D-69451 Weinheim, 1996)).

The process in accordance with the invention enables the catalyst used to be separated readily and to be reused several times.

Advantages in the use of the catalyst in the process in accordance with the invention are, in addition to high yields of (all-rac.)-α-tocopherol, the avoidance of corrosion, the avoidance of waste water contamination with heavy metal ions, high selectivity, and easy isolation of the (all-rac.)-α-tocopherol product from the mixture after reaction.

The following examples are provided to further illustrate the process of the present invention. These examples are illustrative only and are not intended to limit the scope of the invention in any way.

EXAMPLES

Example 1

5.23 g (33 mmol) of trimethylhydroquione (TMHQ) were suspended/dissolved in 50 ml of toluene, whereafter 6.8 mg of tris(trifluoromethanesulphonyl)methane were added and the mixture was heated to about 100° C. To the heated mixture with stirring there was added portionwise 6 ml (16.5 mmol) of isophytol over a period of about 60 minutes. Subsequently, the reaction mixture is stirred for a further 30 minutes at 100° C., after which the reaction was determined, by gas chromatography (GC), to have been completed.

To isolate the crude (all rac.)-α-tocopherol formed in the reaction the solvent was evaporated off under reduced pressure.

This produced 6.52 g (91.7% theoretical yield) of (all-rac.)-α-tocopherol, as analyzed by GC.

If desired, the crude product can be converted into its acetate by standard procedures.

Example 2

7.69 g (49.5 mmol) of trimethylhydroquione were suspended/dissolved in a two-phase solvent system consisting 50 ml of heptane and 40 ml of ethylene carbonate, whereafter 13.6 mg of tris(trifluoromethanesulphonyl)methane were added and the mixture was heated to about 95° C. To the stirred, heated mixture 11.88 ml (33 mmol) of isophytol were added over a period of about 20 minutes. Subsequently, the reaction mixture was stirred for a further 30 minutes at 95° C., after which the reaction was determined by GC to have been completed.

To isolate the crude (all-rac.)-α-tocopherol formed in the reaction, the heptane was evaporated off by concentration under reduced pressure. The remaining ethylene carbonate phase was then cooled to about 80° C. and extracted with 50 ml of fresh heptane. After the phase separation, the heptane phase containing the product was evaporated under a reduced pressure of 20 mbar (2 kPa) at 40° C. (The separated off ethylene carbonate phase, containing the catalyst can be reused if desired).

This produced 13.27 g (96.6% theoretical yield) of (all-rac.)-α-tocopherol, as analyzed by GC.

If desired, the crude product can be converted into its acetate by standard procedures.

Example 3

(all-rac.)-α-tocopherol was produced according to the method set forth in Example 2, with the exception that 40 ml of propylene carbonate were substituted for 40 ml of ethylene carbonate as the co-solvent. This produced 13.27 g (93.4% theoretical yield) of (all-rac.)-α-tocopherol.

Example 4

7.69 g (49.5 mmol) of trimethylhydroquinone were dissolved in 40 ml of ethylene carbonate at 90° C. After addition of 50 ml of heptane, 0.52 g (1.0 mmol) of silver tris(trifluoromethanesulphonyl)methide [$(CF_3SO_2)_3CAg$] were also added to the mixture. Over a period of 20 minutes, 11.88 ml (33 mmol) of isophytol were introduced into the mixture at 94° C. After stirring for 30 minutes, the mixture was extracted with 50 ml of fresh heptane. (After phase separation, the carbonate phase can be reused if desired). The heptane phase was concentrated under a reduced pressure of 20 mbar (2 kPa) at 40° C., and the crude product analyzed by GC. The yield of (all-rac.)-α-tocopherol was 12.79 g (90% theoretical yield).

Example 5

7.69 g (49.5 mmol) of trimethylhydroquinone were dissolved in 40 ml of ethylene carbonate at 90° C. After addition of 50 ml of heptane, 0.17 g (0.33 mmol) silver tris(trifluoromethanesulphonyl)methide was also added to the mixture. Over a period of 20 minutes, 11.88 ml (33 mmol) of isophytol were introduced into the mixture at 94° C. After stirring for 30 minutes, the heptane was distilled off, the reaction mixture cooled to 80° C., and the ethylene carbonate phase extracted with 50 ml of fresh heptane. (After phase separation, the ethylene carbonate phase can be reused if desired). The heptane phase was concentrated under a reduced pressure of 20 mbar (2 kPa) at 40° C. and the crude product analyzed by GC. The yield of (all-rac.)-α-tocopherol is 12.43 g (87.5% theoretical yield).

Example 6

7.69 g (49.5 mmol) trimethylhydroquione were dissolved in 40 ml of ethylene carbonate at 90° C. After addition of 50 ml of heptane, 0.69 g (0.33 mmol) of zirconium tris(trifluoromethanesulphonyl)methide ([(CF₃SO₂)₃C]₄Zr) was also added to the mixture. Over a period of 20 minutes, 11.88 ml (33 mmol) of isophytol were introduced into the mixture at 94° C. After stirring for 30 minutes, the heptane was distilled off, the reaction mixture cooled to 80° C., and the ethylene carbonate phase extracted with 50 ml of fresh heptane. (After phase separation, the ethylene carbonate phase can be reused if desired). The heptane phase was concentrated under a reduced pressure of 20 mbar (2 kPa) at 40° C. and the crude product analyzed by GC. The yield of (all-rac.)-α-tocopherol was 12.8 g (90.06% theoretical yield).

Example 7

7.69 g (49.5 mmol) trimethylhydroquinone were dissolved in 40 ml of ethylene carbonate at 90° C. After addition of 50 ml of heptane, 0.292 g (0.33 mmol) of copper tris(trifluoromethanesulphonyl)methide ([(CF₃SO₂)₃C]₂Cu) were also added to the mixture. Over a period of 20 minutes, 11.88 ml (33 mmol) of isophytol were introduced into the mixture at 94° C. After stirring for 30 minutes, the heptane was distilled off, the reaction mixture cooled to 80° C., and the ethylene carbonate phase extracted with 50 ml of heptane. (After phase separation, the ethylene carbonate phase can be reused if desired). The heptane phase was concentrated under a reduced pressure of 20 mbar (2 kPa) at 40° C. and the crude product analyzed by GC. The yield of (all-rac.)-α-tocopherol was 13.33 g (93.80% theoretical yield).

Example 8

4.4 g (28.3 mmol) trimethylhydroquinone were dissolved in 23 ml of ethylene carbonate at 90° C. After addition of 30 ml of heptane, 0.16 g (0.18 mmol) of vanadyl tris(trifluoromethanesulphonyl)methide ([(CF₃SO₂)₃C]₂VO) were added. Over a period of 20 minutes, 6.8 ml (18.9 mmol) of isophytol were introduced into the mixture at 94° C. After stirring for 30 minutes, the heptane was distilled off, the reaction mixture cooled to 80° C., and the carbonate phase extracted with 30 ml heptane. (After phase separation, the ethylene carbonate phase can be reused if desired). The heptane phase was concentrated under a reduced pressure of 20 mbar (2 kPa) at 40° C. and the crude product analyzed by GC. The yield of (all-rac.)-α-tocopherol was 7.46 g (91.7% theoretical yield).

Example 9

7.69 g (49.5 mmol) trimethylhydroquinone were dissolved in 40 ml ethylene carbonate at 90° C. After addition of 50 ml heptane, 0.582 g (0.33 mmol) of tin tris(trifluoromethanesulphonyl)methide ([(CF₃SO₂)₃C]₄Sn) were added. Over a period of 20 minutes, 11.88 ml (33 mmol) of isophytol were introduced into the mixture at 94° C. After stirring for 30 minutes, the heptane was distilled off, the reaction mixture cooled to 80° C., and the carbonate phase extracted with 30 ml of heptane. (After phase separation, the ethylene carbonate phase can be reused if desired). The heptane phase was concentrated under a reduced pressure of 20 mbar (2 kPa) at 40° C. and the crude product analyzed by GC. The yield of (all-rac.)-α-tocopherol was 12.74 g (89.67% theoretical yield).

The invention being thus described, it will be obvious that the same may be varied in many ways. Such variations are not to be regarded as a departure from the spirit and scope of the invention and all such modifications are intended to be included within the scope of the following claims.

What is claimed is:

1. A method of making (all-rac.)-α-tocopherol comprising:

a) reacting trimethylhydroquinone (TMHQ) with isophytol (IP) or phytol (PH) in an organic solvent and in the presence of a tris(perfluoroalkanesulphonyl)methane, a tris(pentafluorobenzenesulphonyl)methane, a metal tris(perfluoroalkanesulphonyl)methide, or a metal tris(pentafluorobenzenesulphonyl)methide catalyst of formula I:

[R¹SO₂)₃C]ₓ R²   I 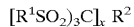

wherein
    R¹ is a perfluoroalkyl group $C_nF_{2n+1}$ or pentafluorophenyl,
    R² is a proton or a metal cation selected from the group consisting of boron, magnesium, aluminium, silicon, scandium, titanium, vanadium, vanadyl, manganese, iron, cobalt, nickel, copper, zinc, yttrium, zirconium, rhodium, palladium, silver, tin, lanthanum, cerium, praseodymium, neodymium, europium, dysprosium, ytterbium, hafnium, platinum, and gold,
    n is an integer from 1 to 10, and
    x is the corresponding valency of the proton (1) or metal cation (1, 2, 3, or 4); and b) isolating the (all-rac.)-α-tocopherol.

2. A method according to claim 1 wherein the organic solvent is selected from the group consisting of aliphatic ketones, cyclic ketones, aliphatic esters, cyclic esters, aliphatic hydrocarbons, and aromatic hydrocarbons.

3. A method according to claim 1 wherein the organic solvent is selected from the group consisting of isobutyl methyl ketone, diethyl ketone, cyclopentanone, isophorone, ethyl acetate, isopropyl acetate, γ-butyrolactone, ethylene carbonate, propylene carbonate, hexane, heptane, octane, benzene, toluene, and xylene.

4. A method according to claim 1 wherein the catalyst is present in the reacting step at from about 0.1 mole % to about 2 mole % based on the amount of TMHQ, IP, or PH present in the reacting step, whichever is used in a lesser molar amount.

5. A method according to claim 1 wherein the reacting step further comprises adding a Bronsted acid as a co-catalyst when the catalyst is a metal tris(perfluoroalkanesulphonyl)methide or a metal tris(pentafluorobenzenesulphonyl)methide.

6. A method according to claim 5 wherein the Bronsted acid is selected from the group consisting of sulfuric acid, phosphoric acid, and p-toluenesulphonic acid.

7. A method according to claim 1 wherein, in the reacting step, about 10–100 ml of the organic solvent are present per 10 mmol IP or PH.

8. A method according to claim 7, wherein about 30–60 ml of the organic solvent are present per 10 mmol of IP or PH.

9. A method according to claim 1 further comprising carrying out the reacting step at a temperature between about 60° C. and about 150° C.

10. A method according to claim 9 wherein the temperature is between about 100° C. and about 120° C.

11. A method according to claim 1 wherein the molar ratio of TMHQ:IP or PH in the reacting step is from about 1.3:1 to about 2.5:1.

12. A method according to claim 11 wherein the molar ratio of TMHQ:IP or PH is from about 1.5:1 to about 2.2:1.

13. A method according to claim 12 wherein the molar ratio of TMHQ:IP or PH is about 2:1.

14. An acid-catalyzed process for producing (all-rac.)-α tocopherol comprising:

(a) forming a reaction mixture comprising trimethylhydroquinone (TMHQ) with isophytol (IP) or phytol (PH), an organic solvent, and a tris(perfluoroalkanesulphonyl)methane, a tris(pentafluorobenzenesulphonyl)methane, a metal tris(perfluoroalkanesulphonyl)methide, or a metal tris(pentafluorobenzenesulphonyl)methide catalyst of formula I:

$$[(R^1SO_2)_3C]_x R^2 \qquad \text{I}$$

wherein $R^1$ is a perfluoroalkyl group $C_nF_{2n+1}$ or pentafluorophenyl, $R^2$ is a proton or a metal cation selected from the group consisting of boron, magnesium, aluminium, silicon, scandium, titanium, vanadium, vanadyl, manganese, iron, cobalt, nickel, copper, zinc, yttrium, zirconium, rhodium, palladium, silver, tin, lanthanum, cerium, praseodymium, neodymium, europium, dysprosium, ytterbium, hafnium, platinum, and gold, n is an integer from 1 to 10, and x is the corresponding valency of the proton (1) or metal cation (1,2,3 or 4); and (b) isolating the (all-rac.)-α-tocopherol.

15. A mixture comprising:

(d) trimethylhydroquinone (TMHQ), (e) isophytol (IP) or phytol (PH) in an organic solvent, and (f) a tris(perfluoroalkanesulphonyl)methane, a tris(pentafluorobenzenesulphonyl)methane, a metal tris(perfluoroalkanesulphonyl)methide, or a metal tris-(pentafluorobenzenesulphonyl)methide catalyst of formula I:

$$[(R^1SO_2)_3C]_x R^2 \qquad \text{I}$$

wherein $R^1$ is a perfluoroalkyl group $C_nF_{2n+1}$ or pentafluorophenyl, $R^2$ is a proton or a metal cation selected from the group consisting of boron, magnesium, aluminium, silicon, scandium, titanium, vanadium, vanadyl, manganese, iron, cobalt, nickel, copper, zinc, yttrium, zirconium, rhodium, palladium, silver, tin, lanthanum, cerium, praseodymium, neodymium, europium, dysprosium, ytterbium, hafnium, platinum, and gold, n is an integer from 1 to 10, and x is the corresponding valency of the proton (1) or metal cation (1,2,3 or 4).

* * * * *

UNITED STATES PATENT AND TRADEMARK OFFICE
CERTIFICATE OF CORRECTION

PATENT NO.    : 6,369,242 B2
DATED         : April 9, 2002
INVENTOR(S)   : Werner Bonrath et al.

It is certified that error appears in the above-identified patent and that said Letters Patent is hereby corrected as shown below:

Column 10,
Line 8, please change "$[R^1SO_2)_3C]_xR^2$" to -- $[(R^1SO_2)_3C]_xR^2$ --.

Signed and Sealed this

Twenty-third Day of July, 2002

*Attest:*

*Attesting Officer*

JAMES E. ROGAN
*Director of the United States Patent and Trademark Office*